US007910008B2

(12) United States Patent
Sommer et al.

(10) Patent No.: US 7,910,008 B2
(45) Date of Patent: Mar. 22, 2011

(54) SEALED STERILE SYSTEM AND METHOD FOR FILTERING BIOLOGICAL OR MEDICAL FLUIDS, IN PARTICULAR WHOLE BLOOD

(75) Inventors: Christian Sommer, Gmunden (AT); Michael Kurz, Hallein-Rif (AT); Gunter Mayer, Salzburg (AT)

(73) Assignee: Fresenius Hemocare Austria GmbH, Eugendorf (AT)

( * ) Notice: Subject to any disclaimer, the term of this patent is extended or adjusted under 35 U.S.C. 154(b) by 768 days.

(21) Appl. No.: 11/632,823

(22) PCT Filed: Jun. 14, 2005

(86) PCT No.: PCT/EP2005/006338

§ 371 (c)(1), (2), (4) Date: Mar. 6, 2007

(87) PCT Pub. No.: WO2006/007906

PCT Pub. Date: Jan. 26, 2006

(65) Prior Publication Data

US 2008/0047898 A1 Feb. 28, 2008

(30) Foreign Application Priority Data

Jul. 21, 2004 (DE) ......................... 10 2004 035 352

(51) Int. Cl.
*B01D 37/00* (2006.01)
*B01D 36/00* (2006.01)

(52) U.S. Cl. ..................... 210/767; 210/252; 210/257.1; 210/257.2; 210/436; 210/472; 604/408; 604/409

(58) Field of Classification Search .................. 210/645, 210/767, 252, 257.1, 257.2, 436, 472; 604/408, 604/409, 411, 412, 415, 416
See application file for complete search history.

(56) References Cited

U.S. PATENT DOCUMENTS 4,898,573 A 2/1990 Takenaka et al. ................ 604/6
5,451,321 A * 9/1995 Matkovich .................... 210/641
5,545,339 A * 8/1996 Bormann et al. ............. 210/806
5,601,730 A * 2/1997 Page et al. ..................... 210/806
(Continued)

FOREIGN PATENT DOCUMENTS

EP 0888789 A1 1/1999
(Continued)

OTHER PUBLICATIONS

International Search Report, dated Dec. 20, 2005, 2 pages.

*Primary Examiner* — John Kim
(74) *Attorney, Agent, or Firm* — Kenyon & Kenyon LLP

(57) ABSTRACT

The invention relates to a sealed, sterile system for filtering fluids, in particular whole blood. The system comprises a first collapsible container for receiving the fluid to be filtered and a second collapsible container for receiving the filtered fluid, both containers interconnected by a fluid line, in which a filter and a third container, for deaeration, are located. The first collapsible container contains a predetermined quantity of air, which is sufficient to ensure that no blood remains in the filter and the adjacent tube line sections when the whole blood is transferred from the first container into the second container. The air that is present in the second container, after the whole blood has been filtered, is transferred to the deaeration container.

18 Claims, 1 Drawing Sheet

U.S. PATENT DOCUMENTS

| | | | | |
|---|---|---|---|---|
| 5,670,060 | A * | 9/1997 | Matkovich et al. | 210/767 |
| 5,776,338 | A | 7/1998 | Mari | 210/252 |
| 6,086,770 | A | 7/2000 | Matkovich | 210/645 |
| 6,190,855 | B1 * | 2/2001 | Herman et al. | 435/2 |
| 6,428,712 | B1 * | 8/2002 | Castino | 210/800 |
| 6,997,893 | B2 * | 2/2006 | Mathias et al. | 604/6.15 |
| 7,351,344 | B2 * | 4/2008 | Verri et al. | 210/767 |
| 2002/0011452 | A1 | 1/2002 | Mari et al. | |

FOREIGN PATENT DOCUMENTS

| | | |
|---|---|---|
| WO | WO9839080 | 9/1998 |
| WO | WO9944718 | 9/1999 |
| WO | WO0062840 | 10/2000 |
| WO | WO0176721 | 10/2001 |
| WO | WO03064000 | 8/2003 |

* cited by examiner

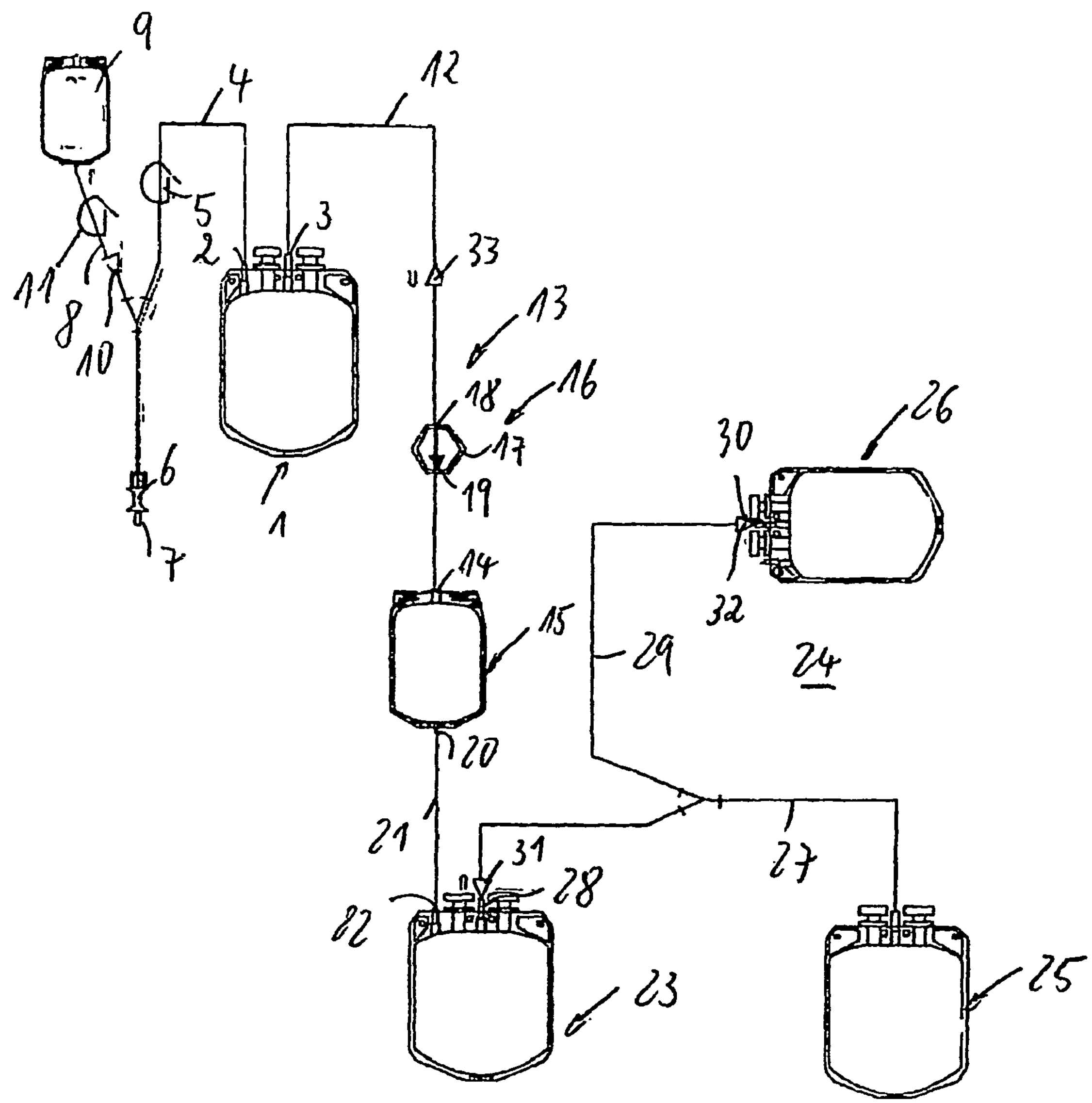
9
4
12
5
3
2
33
11
8
10
13
18
16
17
19
6
7
1
26
30
32
14
15
29
24
20
21
27
31
28
22
23
25

SEALED STERILE SYSTEM AND METHOD FOR FILTERING BIOLOGICAL OR MEDICAL FLUIDS, IN PARTICULAR WHOLE BLOOD

FIELD OF THE INVENTION

The present invention relates to a sealed sterile system for filtering biological and medical fluids, in particular whole blood, and a method for filtering biological and medical fluids, in particular whole blood.

BACKGROUND OF THE INVENTION

European patent document EP 0 349 188 B1 describes a device for the separation of blood into blood components, which has a blood collection bag which is connected via a first tube line to a primary bag, whereby the primary bag is connected via a further tube line to a satellite bag. A filter for the removal of leucocytes is disposed in the first tube line, which connects the blood collection bag to the primary bag. In order to obtain leucocyte-free components, a donor's whole blood is collected in the blood collection bag and transferred via the tube line containing the filter into the primary bag. The section of the tube line lying between the filter and the primary bag is then severed, whereby the severing point is sealed off. The primary bag is then centrifuged together with the secondary bag in order to separate the blood in the primary bag into two blood components. One of the two blood components is then transferred via the second tube line into the satellite bag. In this way, leucocyte-free blood components can be obtained after filtration of the whole blood. A decisive advantage with the known method is seen in the fact that centrifugation of the bag arrangement takes place without the filter and a mechanical strain on the filter is thus avoided.

The device for filtering whole blood known from European patent document EP 0 349 188 B1 is disadvantageous in that, after the completion of the filtration process, i.e., after the whole blood has ceased to flow from the blood collection bag into the primary bag under the influence of gravity, fluid can still remain in the leucocyte filter and in the respective tube line sections.

International Publication Number WO 91/17809 describes a filtering system which comprises a collection bag for receiving the filtered fluid, said collection bag being connected via a tube line, in which a filter is disposed, to a receiving bag containing the fluid to be filtered. The fluid to be filtered is transferred, under the influence of gravity, from the receiving bag via the tube line and the filter into the collection bag. In order to recover the fluid remaining in the filter and the adjacent tube line sections after completion of the filtration process, there is provided on the tube line a gas inlet upstream of the filter and a gas outlet downstream of the filter. After completion of the filtration process, gas is conveyed via the inlet into the system, said gas being carried away again via the outlet thereby expelling the fluid present in the system. In a preferred embodiment of the known filtering system, the gas to be conveyed into the system after completion of the filtration process is made available in a flexible bag, which is connected via a tube line to a gas inlet. The air carried away from the system is collected in a second flexible bag, which is connected via a second tube line to the gas outlet. In order to recover the fluid present in the system, the first bag is compressed after completion of the filtration process, as a result of which the gas flows into the system thereby expelling the fluid. The drawback is that the known filtering system with the gas inlet and the outlet is relatively costly to produce and difficult to manage.

There is also known from International Publication Number WO 03/064000 A1 a filtering device which comprises a filter. The filtering device has a tube line, which connects a receiving bag to a collection bag and into which a filter is incorporated, which is divided by a filter material into a first and second chamber. Moreover, the device has another bag, which is in a flow connection with the first and second filter chamber respectively via an air inlet and outlet line. Disposed in one of the two lines is a non-return valve, which permits a passage of fluid only in the direction of the first filter chamber. The bag serves for deaeration of the system when the fluid is transferred from the receiving bag into the collection bag. The drawback is that the incorporation of the bag with the air inlet and outlet lines makes the handling of the system difficult.

SUMMARY OF THE INVENTION

An objective of the present invention is to make available a sealed sterile system for filtering biological and medical fluids, in particular whole blood, which can easily be managed and produced at relatively low cost. A further objective of the present invention is to provide a filtering method for filtering biological or medical fluids that is easy to implement.

According to the sealed sterile filtering system and the method according of the present invention, the air that is required for complete emptying of the filter and the adjacent tube line sections during the transfer of the fluid to be filtered from the first collapsible container through the filter into the second collapsible container is made available in the first collapsible container. The filtering system and method according to the invention are thus fundamentally different from the known systems and methods, wherein the bag for receiving the whole blood is completely filled with an anticoagulant. With the device and the method according to the invention, therefore, there is no need for the otherwise required sucking-out of air present in the blood collection bag filled with anticoagulant.

In order to guarantee complete deaeration, the preset quantity of air should be greater than the volume of the filter and the adjacent tube line sections. Apart from the air present in the first container, the air present in the adjacent line sections can also be used for the deaeration of the system.

The quantity of air preset in the first collapsible container is transferred together with the fluid to be filtered into the second collapsible container, while the filter and the adjacent tube line sections are completely emptied. A particular advantage lies in the fact that only relatively small forces are required for the transfer of the fluid. The transfer of the fluid can take place under the influence of the gravitational force of the first collapsible container. Further steps are not required for the transfer of the fluid.

The filtering system according to the invention has a third collapsible container, whose filling volume is less than the filling volume of the first or second collapsible container. After the transfer of the fluid from the first into the second collapsible container, the air present in the second collapsible container can be transferred into the third collapsible container. The second collapsible container is thus completely deaerated. The third collapsible container can, however, also be used for sampling if a part of the fluid present in the third container is also transferred into the second container.

The filling volume of the third collapsible container should be greater than the volume of the filter and the adjacent tube sections, so that the quantity of air required for the deaeration can be transferred completely from the second container into the third container.

According to an embodiment of the invention, the first collapsible container is a collection bag for whole blood, which is filled, preferably up to the preset quantity of air, with a fluid, in particular an anticoagulant.

For the collection of the fluid to be filtered, the first collapsible container preferably has an inlet, to which an openable collection line leads. The openable collection line is preferably a blood removal line with a needle, which is closed by a tube clamp.

Another embodiment also provides, apart from the three containers, a satellite container arrangement, which contains one or more satellite containers. The satellite container arrangement permits the separation of the filtered whole blood into further components according to the known methods.

The collapsible containers are preferably bags made from flexible film. Such bags belong to the prior art.

BRIEF DESCRIPTION OF THE DRAWINGS

FIG. 1 schematically illustrates the filtering system according to an embodiment of the present invention.

DETAILED DESCRIPTION OF THE DRAWINGS

In the following exemplary embodiments a device and method in accordance with the present invention is explained in greater detail by reference to FIG. 1.

The sealed sterile system for filtering whole blood comprises a first collapsible container 1, which has an inlet 2 and an outlet 3. The collapsible container is a conventional bag made from a flexible film. In the example embodiment, the other containers that the system comprises are also film bags.

Connected to inlet 2 of blood collection bag 1 is a blood removal line 4, which is closed by a tube clamp 5. Connected via an adapter 6 to the free end of blood removal line 4 is a needle 7, which serves to remove the whole blood from the donor. Branching off from blood removal line 4 between adapter 6 with needle 7 and tube clamp 5 is a supply line 8, which leads to the outlet of a first sampling bag 9. Supply line 8 is closed with a break-off part 10, which makes it possible to produce a flow connection by breaking off a valve piece. Such break-off parts belong to the prior art. Moreover, supply line 8 is closed with a tube clamp 11, which also makes it possible to interrupt the flow connection after the breaking-off of the valve piece of break-off part 10.

Departing from outlet 3 of blood collection bag 1 is a first section 12 of a whole blood line 13, which leads to an inlet 18 of a leucocyte filter 16 for the filtration of the whole blood, which has a housing 17 which is divided by a filter material into two chambers (not shown). Departing from an outlet 19 of filter 17 is a second section 21 of blood line 13, which leads to an inlet 22 of a bag 23 for receiving the filtered whole blood. Disposed in the second section 21 of blood line 13 is a deaeration bag 15, which has an inlet 14 and an outlet 20.

The sterile system also comprises a satellite container arrangement 24, which contains one or more satellite containers. In the example embodiment, satellite container arrangement 24 contains a satellite bag 25 and an additive bag 26, which is filled with an additive solution. First satellite bag 25 is connected via a satellite line 27 to an outlet 28 of bag 23. Branching off from the satellite line 27 is a further transfer line 29, which leads to an inlet/outlet 30 of bag 26. Satellite and transfer line 27 and 29 are again closed with known break-off parts 31, 32, so that, before the breaking-off of the break-off part, satellite container arrangement 24 is separated from bag 23 for receiving the filtrated fluid.

Deaeration bag 15 has a filling volume which is smaller than the filling volume of blood collection bag 1 or bag 23 for receiving the filtered blood. The filling volume of deaeration bag 15 is in any event greater than the volume that is enclosed by the two chambers of filter 16, first and second section 12, 21 of blood line 13, blood removal line 4 and the section of supply line 8 downstream of break-off part 10.

Disposed between blood collection bag 1 and filter 16 is a further break-off part 33, which closes blood line 13. Needle 7 is sealed sterile before use of the filtering system, so that the arrangement forms a sterile sealed system.

Blood collection bag 1 is filled, up to a preset quantity of air, with an anticoagulant. First section 12 of blood line 13 is first severed in manufacture. The anticoagulant is filled via section 12 of blood line 13 connected to blood collection bag 1. During filling the fluid column is allowed to flow back to just before the inlet of bag 1, before the sections of blood line 13 are connected to one another via break-off part 33. Since vacuum suction is dispensed with during the filling, air still remains in the tube lines beside the air bubble in bag 1. Deaeration bag 15 preferably contains no air. The other bags also preferably contain no air.

After the puncture, tube clamp 5 is opened in order to remove whole blood, so that whole blood flows from the donor into blood collection bag 1 filled with the anticoagulant. The blood thereby pushes the air present in the respective tube line sections into blood collection bag 1.

The break-off piece of break-off part 33 is then broken off, so that a flow connection is produced between blood collection bag 1 and bag 23 for receiving the filtered whole blood. The whole blood is transferred together with the air present in bag 1 through filter 16 via deaeration bag 15 into bag 23. Since the air present in bag 1 is sufficient to deaerate the system, no residual fluid remains in the two chambers of filter 16 and the respective tube line sections and deaeration bag 15. The whole blood freed from leucocytes is now present in bag 23. The transfer of the whole blood can take place solely under gravitational force.

The residual air present in bag 23 can be transferred into deaeration bag 15. For this purpose, bag 23 is compressed, so that the air passes via second section 21 of blood line 13 into bag 15. Deaeration bag 15 can serve not only to deaerate the system, but also to remove samples for quality controls. Deaeration bag 15 has a volume of 60 ml in the example embodiment.

Bag 23, containing the leucocyte-free whole blood, can then be separated together with satellite container arrangement 24 from the remaining components of the filtering system in order to obtain individual blood components from the whole blood by centrifugation in the known manner.

The invention claimed is:

1. A sealed sterile system for filtering fluids, comprising:

a first collapsible container configured to receive a fluid for filtration, a filter including a housing, the housing divided by a filter material into a first chamber having an inlet and a second chamber having an outlet, a second collapsible container configured to receive the fluid after filtration, a first section of a fluid line leading from an outlet of the first collapsible container to the inlet of the filter and a second section of the fluid line leading from the outlet of the filter to an inlet of the second collapsible container, and a third collapsible container disposed in the second section of the fluid line that is configured to deaerate the second collapsible container, wherein before filtering the fluid the first collapsible container contains a preset quantity of air, and the third collapsible container contains no air, and wherein the filling volume of the third collapsible container is smaller than the filling volume of at least one of the first collapsible container and the second collapsible container, and is greater than the volume that is enclosed by the two chambers of the filter, the first section of the fluid line, and second section of the fluid line.

2. The sterile system according to claim 1, wherein the first collapsible container is filled, up to the preset quantity of air, with a fluid.

3. The sterile system according to claim 1, wherein the first collapsible container includes an inlet to which an openable collection line leads.

4. The sterile system according to claim 3, wherein the collection line is a blood removal line including a needle and a tube clamp, the blood removal line closable by the tube clamp.

5. The sterile system according to claim 1, wherein the second collapsible container includes an outlet from which a satellite line leads to a satellite container arrangement, the satellite container arrangement containing at least one satellite container.

6. The sterile system according to claim 1, wherein the first collapsible container is a collection bag for whole blood.

7. The sterile system according to claim 6, wherein the blood collection bag is filled with an anticoagulant.

8. The sterile system according to claim 1, wherein the filter is a leucocyte filter.

9. The sterile system according to claim 1, wherein before use, the second collapsible container contains no air.

10. The sterile system according to claim 1, wherein the preset quantity of air is greater than the volume of the filter and the first section of the fluid line and the second section of the fluid line.

11. A method for filtering liquids, comprising collecting a fluid to be filtered in a first collapsible container, the first collapsible container containing a preset quantity of air before filtering, transferring the fluid and the preset quantity of air from the first collapsible container through a filter into a second collapsible container, wherein a first section of a fluid line leads from an outlet of the first collapsible container to an inlet of the filter and a second section of the fluid line leads from an outlet of the filter to an inlet of the second collapsible container, and then transferring the preset quantity of air from the second collapsible container into a third collapsible container, the third collapsible container containing no air before collecting the fluid, wherein the third collapsible container has a filling volume that is smaller than the filling volume of at least one of the first collapsible container and the second collapsible container, and is greater than the volume that is enclosed by the filter, the first section of the fluid line, and second section of the fluid line.

12. The method according to claim 11, wherein the fluid to be filtered is whole blood.

13. The method according to claim 12, wherein, before the collection of whole blood, the first collapsible container is filled, up to the preset quantity of air, with an anticoagulant.

14. The method according to claim 12, wherein before use, the second collapsible container contains no air.

15. The method according to claim 12, wherein the preset quantity of air is greater than the volume of the filter and the first and second sections of the fluid line on either side of the filter.

16. The method according to claim 11, wherein the filter is a leucocyte filter.

17. The method according to claim 11, wherein the third collapsible container is disposed in the second section of the fluid line.

18. The method according to claim 11, wherein the fluid and the preset quantity of air is transferred from the first collapsible container, through the third container, into the second container.

* * * * *